United States Patent
Ueda et al.

(10) Patent No.: US 10,500,390 B2
(45) Date of Patent: Dec. 10, 2019

(54) MEDICAL CONNECTOR

(71) Applicant: TERUMO KABUSHIKI KAISHA, Tokyo (JP)

(72) Inventors: Yasuhiro Ueda, Kofu (JP); Takeshi Toyama, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 190 days.

(21) Appl. No.: 15/709,677

(22) Filed: Sep. 20, 2017

(65) Prior Publication Data
US 2018/0008813 A1    Jan. 11, 2018

Related U.S. Application Data

(63) Continuation of application No. PCT/JP2016/001607, filed on Mar. 18, 2016.

(30) Foreign Application Priority Data

Mar. 20, 2015 (JP) ................. 2015-057636

(51) Int. Cl.
*A61M 39/10* (2006.01)
*A61M 39/22* (2006.01)
*A61M 39/04* (2006.01)

(52) U.S. Cl.
CPC ........ *A61M 39/1011* (2013.01); *A61M 39/04* (2013.01); *A61M 39/10* (2013.01);
(Continued)

(58) Field of Classification Search
CPC .. A61M 2039/1083; A61M 2039/1088; A61M 2039/1016; A61M 39/22;
(Continued)

(56) References Cited

U.S. PATENT DOCUMENTS

| | | | | |
|---|---|---|---|---|
| 2012/0029483 | A1* | 2/2012 | Griffith | A61J 15/0015 604/535 |
| 2013/0167841 | A1* | 7/2013 | Sheffer | A61M 16/0816 128/202.27 |
| 2014/0154004 | A1* | 6/2014 | Agate | F16B 21/04 403/349 |

FOREIGN PATENT DOCUMENTS

| | | |
|---|---|---|
| JP | 2004-000483 | 1/2004 |
| JP | 2006-223583 | 8/2006 |

(Continued)

OTHER PUBLICATIONS

International Search Report issued in International Application No. PCT/JP2016/001607 dated Jun. 7, 2016.

*Primary Examiner* — Bhisma Mehta
*Assistant Examiner* — Nidah M Hussain
(74) *Attorney, Agent, or Firm* — Foley & Lardner LLP

(57) ABSTRACT

A medical connector of the present invention is characterized in that: when a male connector portion is inserted into a female connector portion, a first locking portion is engaged with the female connector portion to achieve a first locked state as well as a second locked state; when the second locked state is released by operation of a second unlock operating portion and the female connector portion is moved in a disengagement direction with respect to the male connector portion, the locking member is moved in the disengagement direction together with the female connector portion while keeping the first locked state; and when the female connector portion is rotated with respect to the male connector portion, the first locked state is released.

19 Claims, 15 Drawing Sheets

(52) U.S. Cl.
CPC ..... *A61M 39/22* (2013.01); *A61M 2039/1016* (2013.01); *A61M 2039/1027* (2013.01); *A61M 2039/1033* (2013.01); *A61M 2205/0216* (2013.01); *A61M 2207/00* (2013.01)

(58) Field of Classification Search
CPC .................. A61M 39/10; A61M 39/04; A61M 2039/1033; A61M 2039/1027; A61M 39/1011; A61M 39/26; A61M 39/1055; Y10T 403/7005; Y10T 403/7007
See application file for complete search history.

(56) References Cited

FOREIGN PATENT DOCUMENTS

| | | |
|---|---|---|
| JP | 2008-173343 | 7/2008 |
| JP | 2012-520742 | 9/2012 |
| WO | WO-2012/128321 | 9/2012 |

* cited by examiner

MEDICAL CONNECTOR

CROSS-REFERENCE TO RELATED APPLICATIONS

The present application is a bypass continuation of PCT Application No. PCT/JP2016/001607, filed on Mar. 18, 2016, which claims priority to Japanese application No. 2015-057636, filed on Mar. 20, 2015, the contents of which are hereby incorporated by reference in their entireties.

BACKGROUND

The present disclosure relates to a medical connector and more specifically, to a medical connector that allows for more surely preventing unintended disengagement of the connector while securing ease of a connecting operation to another medical connector.

In the related art, a medical connector is used to connect a flow path in an infusion set adapted to inject medical solution into a patient, other medical instruments, and the like. Such a medical connector is normally connected by inserting a male connector portion provided in one connector into a female connector portion provided in the other connector. Additionally, it is common to provide an engagement portion between the connectors in order to prevent unintended disengagement of the connectors. For example, in a Luer-lock connector, a screw is used as an engagement portion, and a two-step connecting operation including inserting a male connector portion into a female connector portion and fastening the same with the screw is required at the time of connection, in which the connecting operation is complicated. Also, when the screw is loosened due to action of external force, there may be a possibility that a connector is unintentionally disengaged.

To solve such a problem, for example, there is a known technique in which a plurality of claws are used as an engagement portion as disclosed in JP 2004-483 A and WO 2012/128321 A1. A medical connector disclosed in JP 2004-483 A and WO 2012/128321 A1 includes a male connector portion and the plurality of claws, and when the male connector portion is inserted into a female connector portion of the other medical connector, the plurality of claws passes over a stepped portion formed in the other medical connector while being elastically deformed, and detachment from the stepped portion is prevented by the claws being restored from the elastic deformation. With this structure, because the connectors can be connected to each other only by inserting the male connector portion into the female connector portion, the connecting operation can be easily performed. Further, because the screw is used as the engagement portion, unintended disengagement of the connectors caused by a loosened screw is prevented.

SUMMARY

However, in a medical connector having a structure as disclosed in JP 2004-483 A and WO 2012/128321 A1, in the case where external force acts on claws in a state in which the medical connector is connected to another medical connector, there may be possibility that the claws pass over a stepped portion in a detachment direction while being elastically deformed and the connectors are unintentionally disengaged.

The concepts described in this application have been developed in view of the above-described situations, and the embodiments described herein are directed to providing a medical connector that can more surely prevent unintended disengagement while securing ease of a connecting operation to another medical connector.

In one embodiment, a medical connector according to the includes: a connector body including a male connector portion and a cover portion surrounding an outer periphery of the male connector portion; a locking member arranged inside the cover portion and movable with respect to the cover portion only within a predetermined range in a direction along an axis line of the male connector portion, and further including a first locking portion; a second locking portion; and a second unlock operating portion, wherein: the first locking portion is engaged with a female connector portion of the other medical connector and capable of bringing the female connector portion into a first locked state; the second locking portion can bring, while in the first locked state, the female connector portion being into a second locked state in which the female connector portion cannot be moved in a disengagement direction with respect to the male connector portion; the second unlock operating portion is an operating portion to release the second locked state; when the male connector portion is inserted into the female connector portion, the first locking portion is engaged with the female connector portion, and the female connector portion is brought into the first locked state and also into the second locked state; when the second locked state is released by operation of the second unlock operating portion and the female connector portion is moved in the disengagement direction with respect to the male connector portion, the locking member is moved in the disengagement direction together with the female connector portion while keeping the first locked state; and when the female connector portion is rotated with respect to the male connector portion, the first locked state is released.

In one aspect, when the male connector portion is inserted into the female connector portion, the locking member is pushed by the female connector portion and moved to a proximal end side of the male connector portion, the locking member is elastically deformed along with this movement, the first locking portion is engaged with the female connector portion along with this elastic deformation, and when the female connector portion is rotated with respect to the male connector portion at the time of releasing the first locked state, the locking member is rotated together with the female connector portion, the locking member is restored from the elastic deformation along with this rotation, and the first locked state is released along with this restoration.

In one aspect, when the male connector portion is inserted into the female connector portion, the locking member is pushed by the female connector portion and is moved to the proximal end side of the male connector portion while being rotated in a first rotating direction, and a direction in which the female connector portion is rotated with respect to the male connector portion at the time of releasing the first locked state is a second rotating direction that is an opposite direction of the first rotating direction.

In one aspect, a first abutting surface is provided on an inner peripheral surface of the cover portion, a second abutting surface is provided on an outer peripheral surface of the locking member, at least one of the first abutting surface and the second abutting surface is formed along a helical trajectory, and the locking member is rotated in the first rotating direction with respect to the male connector portion when the second abutting surface is pressed against the first abutting surface.

In one aspect, the first locking portion is formed as a plurality of engagement portions provided on distal end sides of a plurality of elastic members, a first inner diameter portion having a first inner diameter and a second inner diameter portion having a second inner diameter more reduced than the diameter of the first inner diameter portion are provided on the inner peripheral surface of the cover portion, and when the locking member is pushed by the female connector portion and moved to the proximal end side of the male connector portion, each of the plurality of elastic members is elastically deformed radially inward along with movement from the first inner diameter portion to the second inner diameter portion, and the first locking portion formed as the plurality of engagement portions is engaged with the female connector portion along with this elastic deformation.

In one aspect, the first locking portion is formed as a plurality of engagement protruding portions provided on the distal end sides of the plurality of elastic members and protruding radially inward, and the first locking portion formed as the plurality of engagement protruding portions can be engaged with a plurality of engagement recessed portions for the first locking portion provided in a recessed manner on an outer peripheral surface of the female connector portion.

In one aspect, the second locking portion brings the female connector portion into the second locked state by engaging the female connector portion with the cover portion.

In one aspect, the second locking portion is formed of an engagement protruding portion provided at the cover portion and protruding radially inward, the second locking portion formed of the engagement protruding portion can be engaged with an engagement recessed portion for the second locking portion provided in a recessed manner on the outer peripheral surface of the female connector portion, and the second unlock operating portion is an operating portion of a swing lever including the second locking portion formed of the engagement protruding portion, and integrally formed with the cover portion.

According to certain embodiments of the present invention, when the male connector portion is inserted into the female connector portion, the first locking portion is engaged with the female connector portion, and the female connector portion is brought into the first locked state and also into the second locked state. Therefore, according to the present invention, it is possible to connect the connectors only by inserting the male connector portion into the female connector portion of the other medical connector. Additionally, since the first locking portion is located inside the cover portion in the connected state, unintended disengagement of the connectors due to external force acting on the first locking portion can be prevented.

Furthermore, according to certain embodiments of the present invention, when the second locked state is released by operation of the second unlock operating portion from the connected state of the connectors and the female connector portion is moved in the disengagement direction with respect to the male connector portion, the locking member is moved in the disengagement direction together with the female connector portion while keeping the first locked state, and when the female connector portion is rotated with respect to the male connector portion, the first locked state can be released. Therefore, according to the present invention, three-step operation including operation of the second unlock operating portion, pulling operation of the female connector portion, and rotating operation of the female connector portion is needed to be performed in order to release connection between the connectors.

Therefore, according to certain embodiments of the present invention, it is possible to provide a medical connector that can more surely prevent unintended disengagement while securing ease of a connecting operation to another medical connector.

BRIEF DESCRIPTION OF THE DRAWINGS

FIG. 1B being a partial cross-sectional view taken along a line B-B in FIG. 1D; FIG. 1C being a partial cross-sectional view along a line C-C in FIG. 1D; and FIG. 1D being a perspective view.

FIG. 2B being a cross-sectional view taken along a line D-D in FIG. 2A; and FIG. 2C being a cross-sectional view taken along a line E-E in FIG. 2A.

FIG. 3B being a cross-sectional view taken along a line F-F in FIG. 3A; and FIG. 3C being a cross-sectional view of a line G-G in FIG. 3A.

FIG. 5B being a partial cross-sectional view taken along a line B-B in FIG. 5D; FIG. 5C being a partial cross-sectional view taken along a line C-C in FIG. 5D; and FIG. 5D being a perspective view.

FIG. 6B being a partial cross-sectional view taken along a line B-B in FIG. 6D; FIG. 6C being a partial cross-sectional view taken along a line C-C in FIG. 6D; and FIG. 6D being a perspective view.

FIG. 7B being a partial cross-sectional view taken along a line B-B in FIG. 7D; FIG. 7C being a partial cross-sectional view taken along a line C-C in FIG. 7D; and FIG. 7D being a perspective view.

FIG. 8B being a partial cross-sectional view taken along a line B-B in FIG. 8D; FIG. 8C being a partial cross-sectional view taken along a line C-C in FIG. 8D; and FIG. 8D being a perspective view.

FIG. 9B being a partial cross-sectional view taken along a line B-B in FIG. 9D; FIG. 9C being a partial cross-sectional view taken along a line C-C in FIG. 9D; and FIG. 9D being a perspective view.

DETAILED DESCRIPTION

Figure 1A:
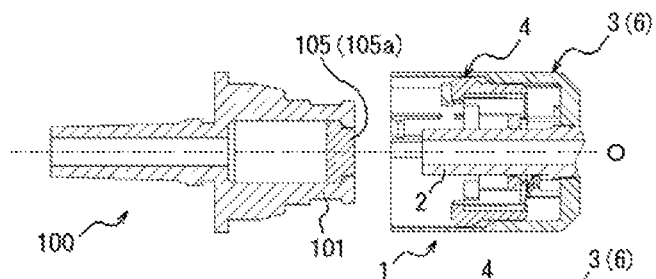
FIGS. 1A-1D depict a medical connector according to an embodiment of the present invention, illustrating a disengaged state from another medical connector, FIG. 1A being a partial cross-sectional view taken along a A-A line in FIG. 1D.
Figure 1B:
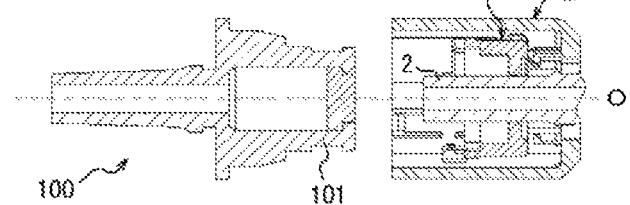
Figure 1C:
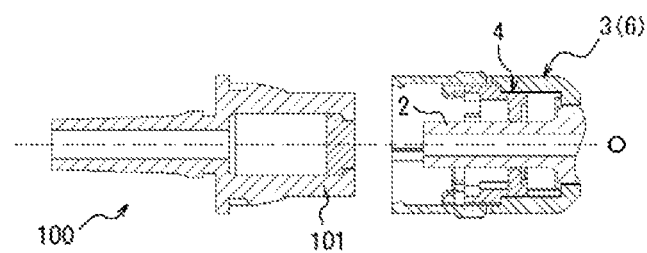
Figure 1D:
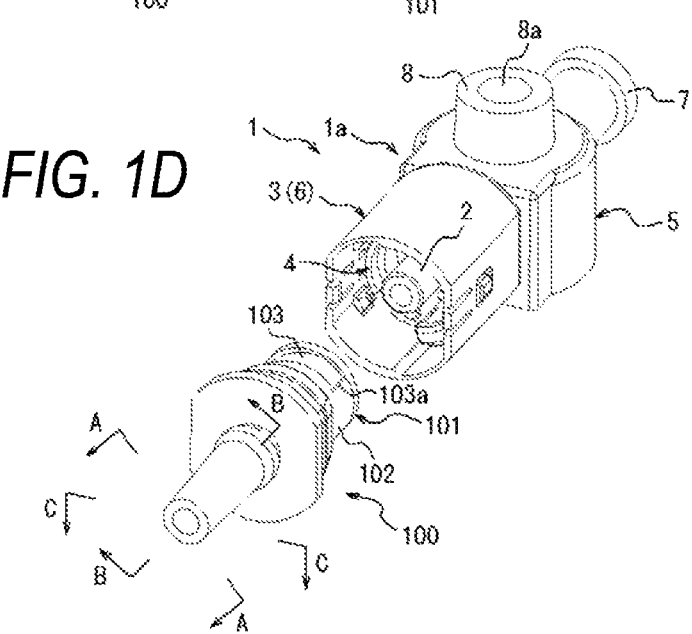

In the following description, a medical connector 1 according to an embodiment of the present invention will be described in detail as an example with reference to FIGS. 1A to 12D.

In the present specification, note that a distal end side refers to a distal end side of a male connector portion 2 in a direction along a center axis line O of the male connector portion 2 of the medical connector 1 (for example, the left side in FIG. 1A), and a proximal end side refers to an opposite side thereof. Additionally, note that a front side refers to the distal end side of the medical connector 1, a rear side refers to the proximal end side of the medical connector 1, a lateral side refers to a lateral direction when viewed from the front side to the rear side, and a vertical side refers to a vertical direction when viewed from the front side to the rear side.

As illustrated in FIGS. 1A to 3, the medical connector 1 according to the present embodiment includes a connector body 1a including the male connector portion 2 and a cover portion 3 surrounding an outer periphery of the male connector portion 2, and a locking member 4 arranged inside the cover portion 3. In the present example, the male connector portion 2 is formed integrally with a housing 5, and the cover portion 3 is formed as a covering member 6 fixed to the housing 5. Additionally, a female connector portion 7 and a mixed injection port portion 8 are formed on the housing 5. While a flow path is formed in an opening portion of the mixed injection port portion 8 by opening the opening portion when a male connector portion of every sort of a medical connector is inserted, a valve body 8a adapted to close the opening portion is provided when the male connector portion is not inserted.

Thus, in the present example, the connector body 1a is formed of: the housing 5 including the male connector portion 2, female connector portion 7, and mixed injection port portion 8; the covering member 6 fixed to the housing 5; and the valve body 8a attached to the mixed injection port portion 8 of the housing 5. The housing 5, covering member 6, locking member 4 can be made of a synthetic resin, for example.

Note that, in the present example, the medical connector 1 is formed as a T-port connector that also includes the female connector portion 7 and the mixed injection port portion 8 in addition to the male connector portion 2, but not limited to this structure. In other words, for example, the medical connector 1 may be formed as a T-shape stopcock further including a flow path switching structure, or may be formed as a male connector directly attached to an end portion of a tube connected to an infusion container or an indwelling needle.

Figure 4A:
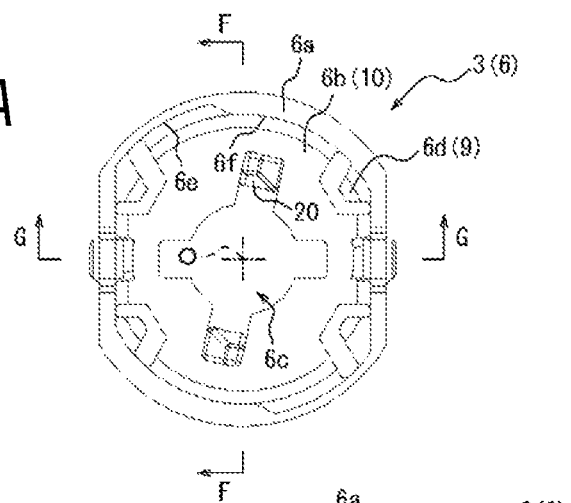
FIGS. 4A-4C depict a covering member of the medical connector illustrated in FIGS. 1A-1D, FIG. 3A being a front view.
Figure 4B:
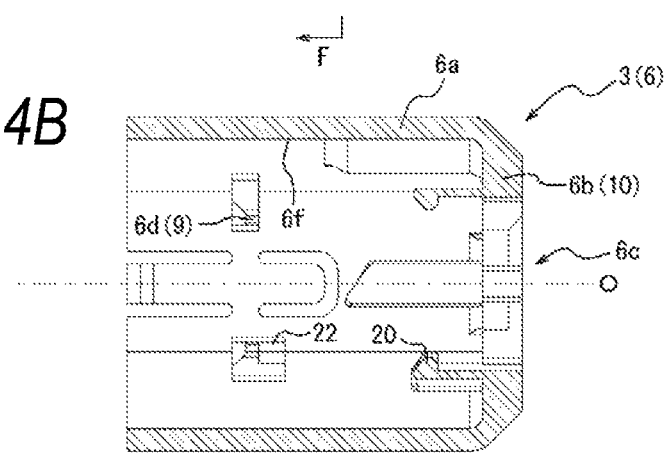
Figure 4C:
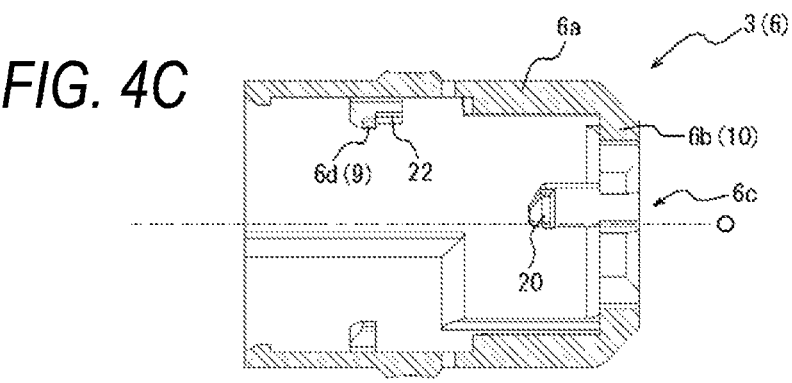

As illustrated in FIG. 4, the covering member 6 includes an outer peripheral wall portion 6a that can surround the locking member 4, and a partition wall portion 6b that partially blocks a proximal end side of the outer peripheral wall portion 6a. A through hole 6c is provided on the partition wall portion 6b, and the partition wall portion 6b can be fitted to a proximal end portion of the male connector portion 2 while allowing the male connector portion 2 to pass through the through hole 6c.

In the present embodiment, the covering member 6 is formed in a manner rotationally symmetric around the center axis line O of the male connector portion 2. A distal-end side stopper portion 9 including a plurality of protrusions 6d (four in the present example) arranged in a circumferential direction at intervals is formed on an inner peripheral surface of the outer peripheral wall portion 6a. Furthermore, a proximal-end side stopper portion 10 is formed of the partition wall portion 6b. When the locking member 4 is arranged inside the covering member 6 by the distal-end side stopper portion 9 and the proximal-end side stopper portion 10, a movement range of the locking member 4 toward the distal end side and the proximal end side is restricted. As a result, the locking member 4 is movable with respect to the covering member 6 only within a predetermined range in the direction along the axis line O of the male connector portion 2. Additionally, a first inner diameter portion 6e having a first inner diameter and a second inner diameter portion 6f having a second inner diameter more reduced than that of the first inner diameter portion 6e are provided on an inner peripheral surface of the covering member 6.

Figure 2A:
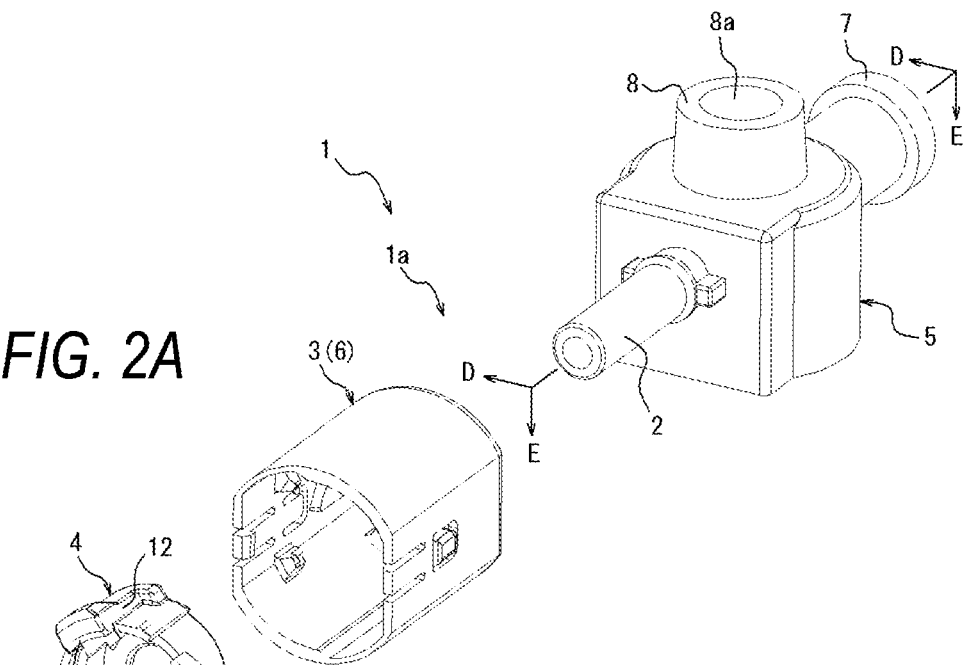
FIGS. 2A-2C depict the medical connector illustrated in FIGS. 1A-1D, FIG. 2A being an exploded perspective view.
Figure 2B:
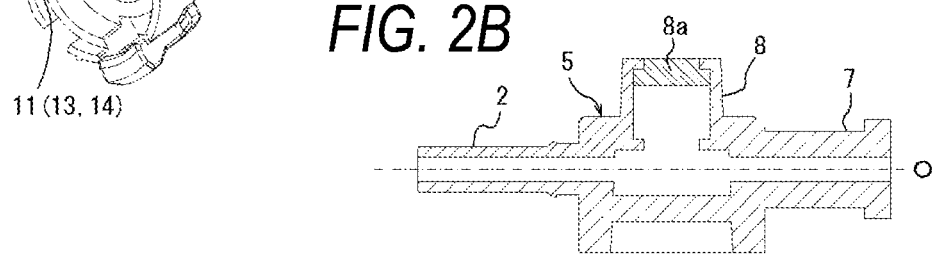
Figure 2C:
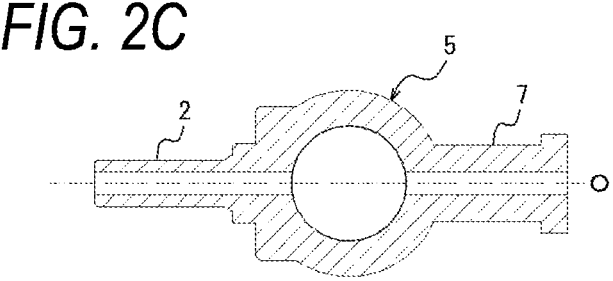
Figure 3:
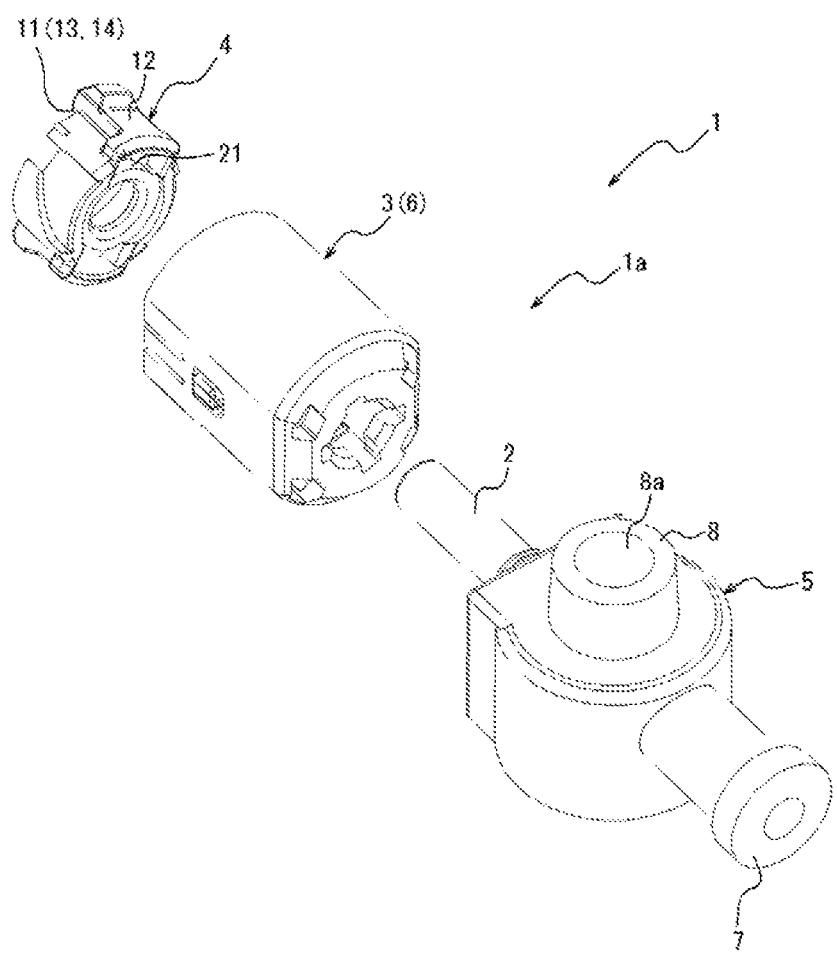
FIG. 3 is an exploded perspective view of the medical connector illustrated in FIG. 1 when viewed from a different angle.
Figure 6A:
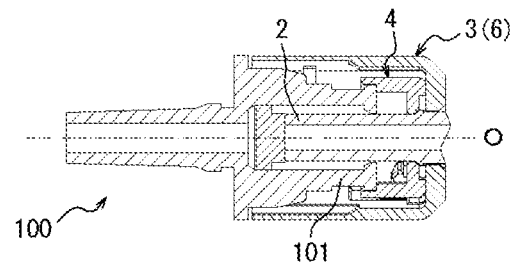
FIGS. 6A-6D depict a state at the time of completing connection between the medical connector illustrated in FIGS. 1A-1D and the other medical connector, FIG. 6A being a partial cross-sectional view taken along a line A-A in FIG. 6D.
Figure 6B:
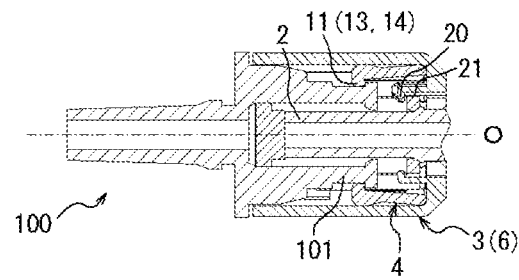

As illustrated in FIGS. 2 and 3, the locking member 4 is formed in a manner rotationally symmetric around the center axis line O of the male connector portion 2 in the present embodiment. Furthermore, the locking member 4 includes a first locking portion 11. As illustrated in FIG. 6B described below, the first locking portion 11 is engaged with a female connector portion 101 of the other medical connector 100, and can bring the female connector portion 101 into a first locked state. In other words, the first locked state refers to a state in which the first locking portion 11 and the female connector portion 101 are engaged.

In the present embodiment, as illustrated in FIGS. 2 and 3, the first locking portion 11 is formed as a plurality of first engagement portions 13 (two in the present example) provided on distal end sides of a plurality of elastic members 12 (two in the present example). More specifically, the plurality of first engagement portions 13 is provided as a plurality of first engagement protruding portions 14 (two in the present example) provided on the distal end sides of the plurality of elastic members 12, and protruding radially inward. The plurality of first engagement protruding portions 14 can be engaged with a plurality of first engagement recessed portions 103 (two in the present example) (engagement recessed portions for the first locking portion) provided in a recessed manner on an outer peripheral surface 102 of the female connector portion 101 of the other medical connector 100 particularly illustrated in FIG. 1D.

Figure 6C:
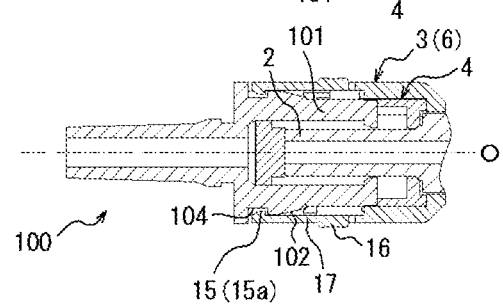
Figure 6D:
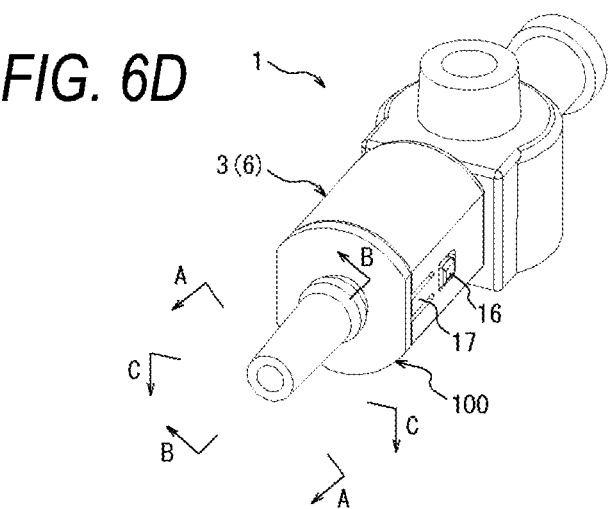
Figure 7A:
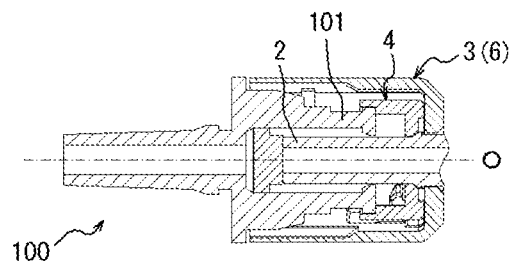
FIGS. 7A-7D depict a state at the time of starting disconnection between the medical connector illustrated in FIGS. 1A-1D and the other medical connector, FIG. 7A being a partial cross-sectional view taken along a line A-A in FIG. 7D.
Figure 7B:
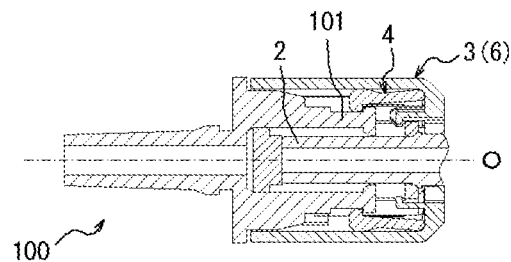
Figure 7C:
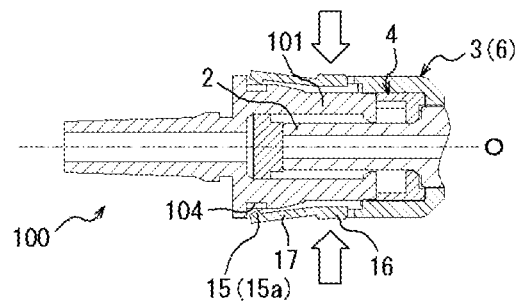
Figure 7D:
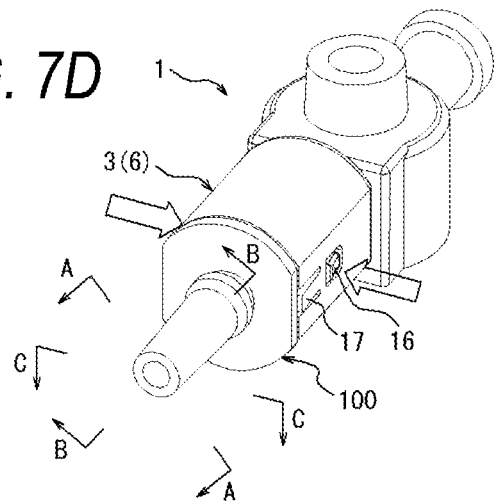
Figure 8A:
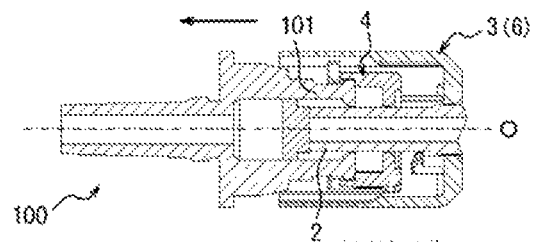
FIGS. 8A-8D depict a state before releasing a first locked state after releasing a second locked state for the medical connector illustrated in FIGS. 1A-1D and the other connector, FIG. 8A being a partial cross-sectional view taken along a line A-A in FIG. 8D.
Figure 8B:
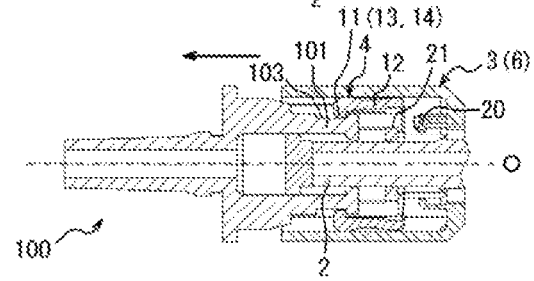
Figure 8C:
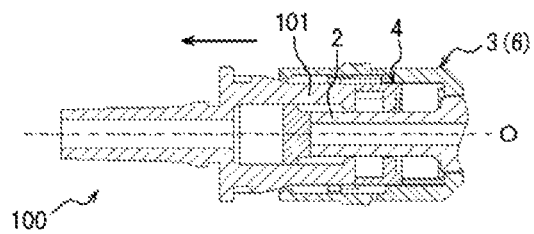
Figure 8D:
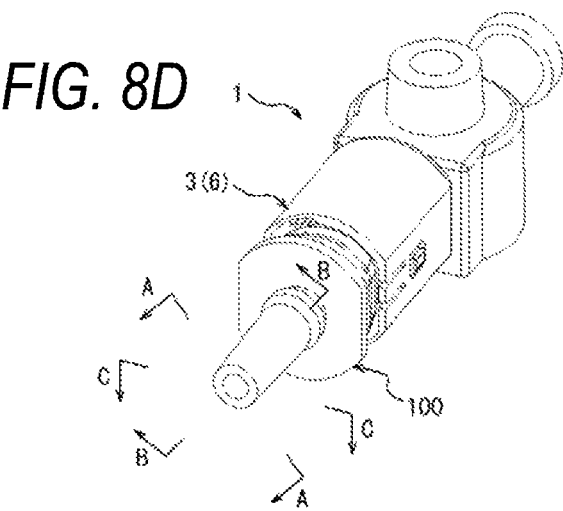

Furthermore, as illustrated in FIG. 6C described later, the medical connector 1 includes a second locking portion 15 and a second unlock operating portion 16. In the first locked state in which the first locking portion 11 is engaged with the female connector portion 101 of the other medical connector 100, the second locking portion 15 can bring the female connector portion 101 into a second locked state (refer to FIG. 6C described later) in which the female connector portion 101 cannot be moved in a disengagement direction with respect to the male connector portion 2. The second unlock operating portion 16 is an operating portion to release the second locked state.

In the present embodiment, the second locking portion 15 is adapted to bring the female connector portion 101 into the second locked state by engaging the female connector portion 101 of the other medical connector 100 with the covering member 6. More specifically, the second locking portion 15 is formed of a second engagement protruding portion 15a provided at the covering member 6 and protruding radially inward, and the second engagement protruding portion 15a can be engaged with a second engagement recessed portion 104 (engagement recessed portion for the second locking portion) provided in a recessed manner on the outer peripheral surface 102 of the female connector portion 101. Furthermore, the second unlock operating portion 16 is an operating portion of a swing lever 17 including the second engagement protruding portion 15a and also integrally provided on the outer peripheral wall portion 6a of the covering member 6. In the present embodiment, the second locking portion 15 and the second unlock operating portion 16 are respectively provided at two places facing each other interposing the axis line O of the male connector portion 2.

Figure 5A:
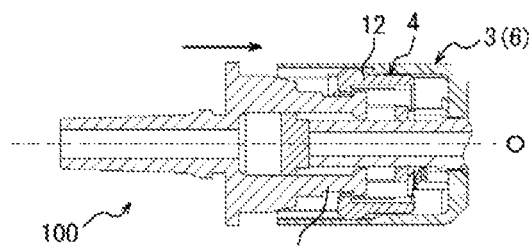
FIGS. 5A-5D depict a state at the time of starting connection between the medical connector illustrated in FIGS. 1A-1D and another medical connector, FIG. 5A being a partial cross-sectional view taken along a line A-A in FIG. 5D.
Figure 5B:
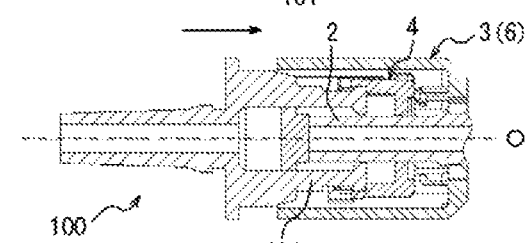
Figure 5C:
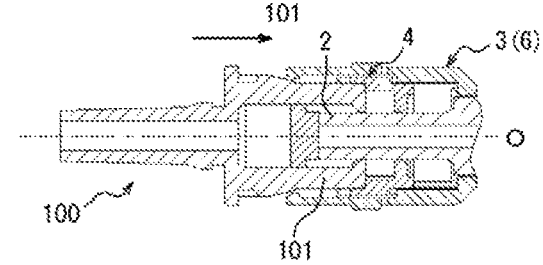
Figure 5D:
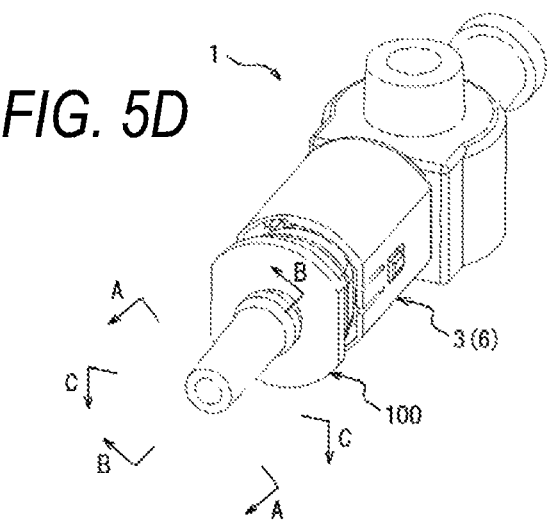

Additionally, the medical connector 1 is adapted to have a structure in which: when the male connector portion 2 is inserted into the female connector portion 101 of the other medical connector 100, the locking member 4 is pushed by the female connector portion 101 and moved to the proximal end side of the male connector portion 2 while being rotated in a first rotating direction as illustrated in FIGS. 5B and 5C; the plurality of elastic members 12 (refer to FIG. 5A) of the locking member 4 is elastically deformed along with this rotation; the first locking portion 11 is engaged with the female connector portion 101 along with this elastic deformation as illustrated in FIGS. 6B and 6C; and the female connector portion 101 is brought into the first locked state and also into the second locked state (in other words, a state in which connection between the male connector portion 2 and the female connector portion 101 is completed).

Furthermore, the medical connector 1 is adapted to have a structure in which connection between the male connector portion 2 and the female connector portion 101 can be released in the following manner. In other words, when the second locked state is released by operation of the second unlock operating portion 16 as illustrated in FIG. 7 and the female connector portion 101 is moved in the disengagement direction with respect to the male connector portion 2 as illustrated in FIG. 8, the locking member 4 is moved in the disengagement direction together with the female connector portion 101 while keeping the first locked state. Then, when the female connector portion 101 is rotated in a second rotating direction that is an opposite direction of the first rotating direction as illustrated in FIG. 9, the locking member 4 is also rotated together with the female connector portion 101, the plurality of elastic members 12 of the locking member 4 is restored from the elastic deformation along with this rotation, and the first locked state is released along with this restoration (completion of disconnection).

Thus, in the medical connector 1, three-step operation including operation of the second unlock operating portion 16, pulling operation of the female connector portion 101, and rotating operation of the female connector portion 101 are needed to be performed in order to release connection to the other medical connector 100. Additionally, a direction of force required in each operation included in the three-step operation is different. Therefore, the medical connector 1 can surely prevent unintended disengagement from the other medical connector 100.

Figure 10A:
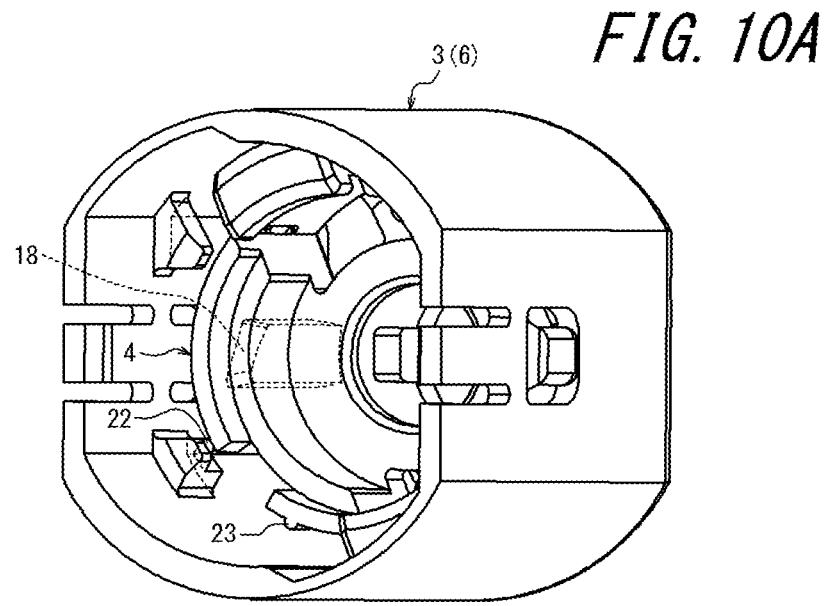
FIG. 10A is a perspective view illustrating the covering member and a locking member in the state at the time of starting connection illustrated in FIG. 5.
Figure 10B:
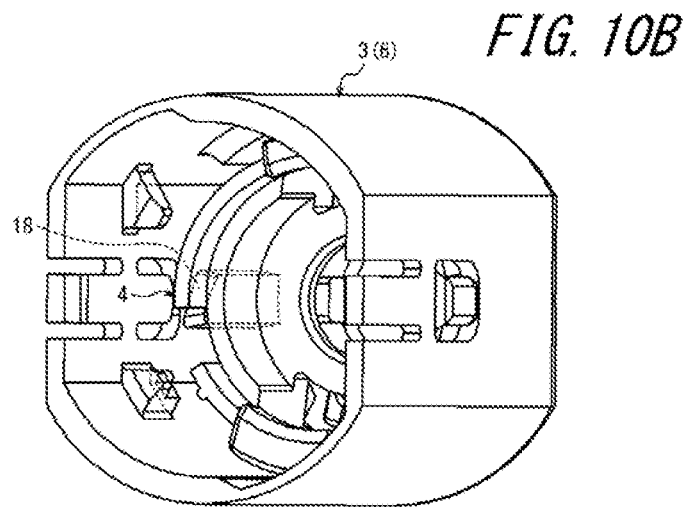
FIG. 10B is a perspective view illustrating the covering member and the locking member in a state between the state at the time of starting connection illustrated in FIG. 5 and the state at the time of completing connection illustrated in FIG. 6.
Figure 10C:
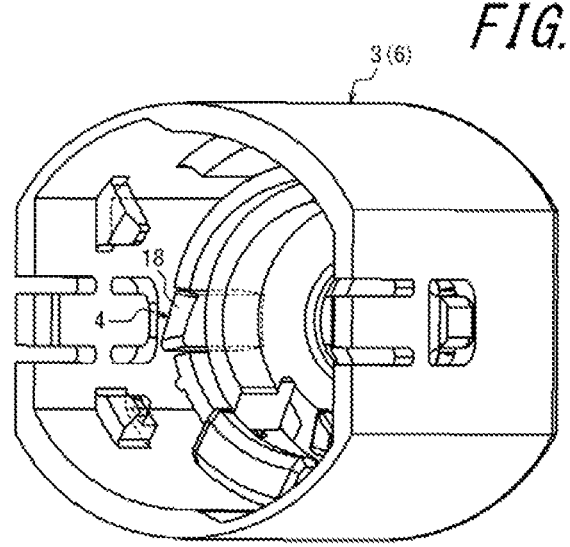
FIG. 10C is a perspective view illustrating the covering member and the locking member in the state at the time of completing connection illustrated in FIG. 6.
Figure 10D:
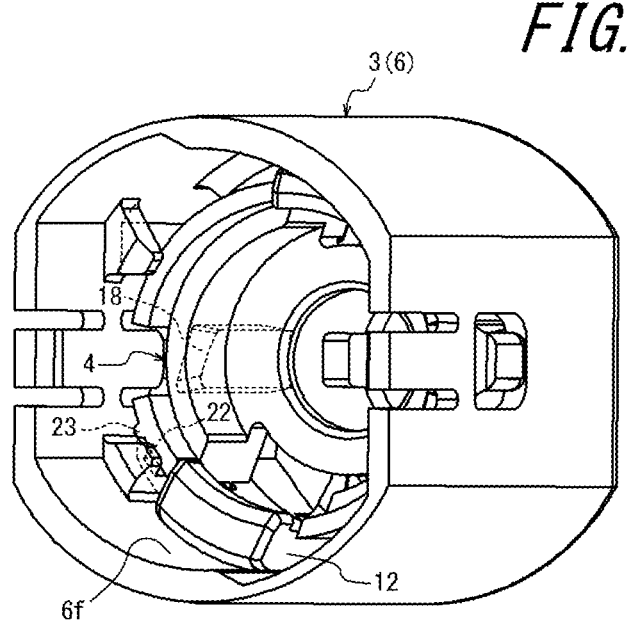
FIG. 10D is a perspective view illustrating the covering member and the locking member in the state before releasing the first locked state after releasing the second locked state illustrated in FIG. 8.

A specific structure in the present embodiment to move, rotate, elastically deform, and restore the locking member 4 will be described below in detail with reference to FIGS. 10A to 12D. FIGS. 10A to 10D are perspective views illustrating the covering member 6 and the locking member 4: FIG. 10A illustrates the state at the time of starting connection illustrated in FIG. 5; FIG. 10B illustrates the state between the state at the time of starting connection illustrated in FIG. 5 and the state at the time of completing connection illustrated in FIG. 6; FIG. 10C illustrates the state at the time of completing connection illustrated in FIG. 6; and FIG. 10D illustrates the state before releasing the first locked state after releasing the second locked state illustrated in FIG. 8.

FIGS. 11A to 11D are perspective views of the covering member 6 and the locking member 4 when viewed from a different angle, and FIGS. 11A to 11D respectively illustrate the states same as those in FIGS. 10A to 10D. Additionally, FIGS. 12A to 12D are side views illustrating the covering member 6 and the locking member 4, and FIGS. 12A to 12D respectively illustrate the states same as those in FIG. 10A to FIG. 10D.

Figure 12A:
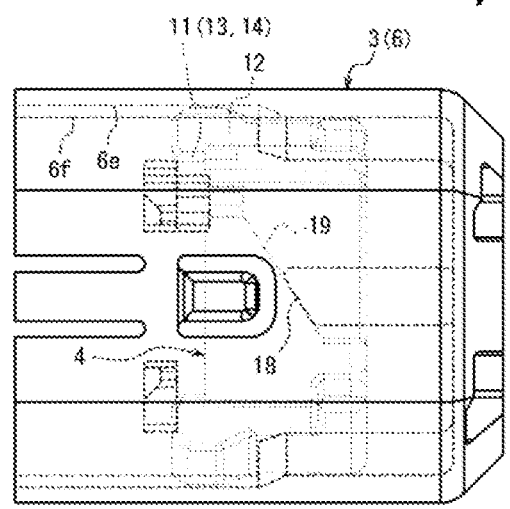
FIG. 12A is a side view illustrating the covering member and the locking member in the state at the time of starting connection illustrated in FIG. 5.
Figure 12B:
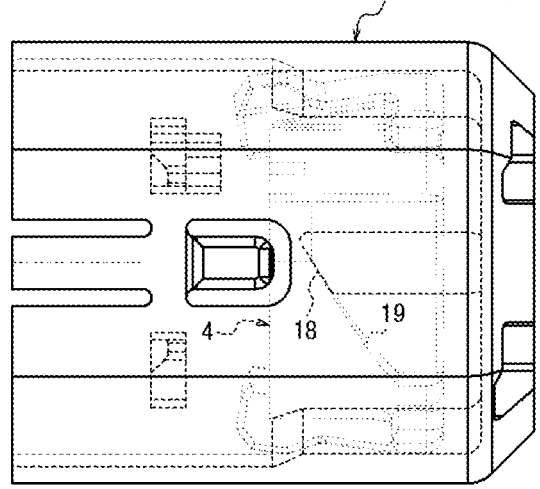
FIG. 12B is a side view illustrating the covering member and the locking member in the state between the state at the time of starting connection illustrated in FIG. 5 and the state at the time of completing connection illustrated in FIG. 6.
Figure 12C:
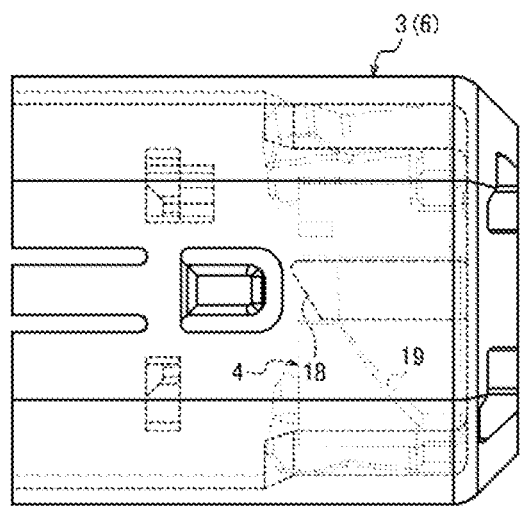
FIG. 12C is a side view illustrating the covering member and the locking member in the state at the time of completing connection illustrated in FIG. 6.

In the present embodiment, a first abutting surface 18 is provided on the inner peripheral surface of the covering member 6 and a second abutting surface 19 is provided on an outer peripheral surface of the locking member 4 as illustrated in FIGS. 12A to 12C in order to rotate the locking member 4. Additionally, at least one of the first abutting surface 18 and the second abutting surface 19 is formed along a helical trajectory. In the present embodiment, more specifically, both of the first abutting surface 18 and the second abutting surface 19 are each formed along a helical trajectory. Additionally, when the locking member 4 is moved to the proximal end side (rear side) with respect to the covering member 6, the second abutting surface 19 is pressed against the first abutting surface 18, thereby rotating the locking member 4 in the first rotating direction (refer to FIGS. 12A to 12C and FIGS. 10A to 10 C).

Figure 11A:
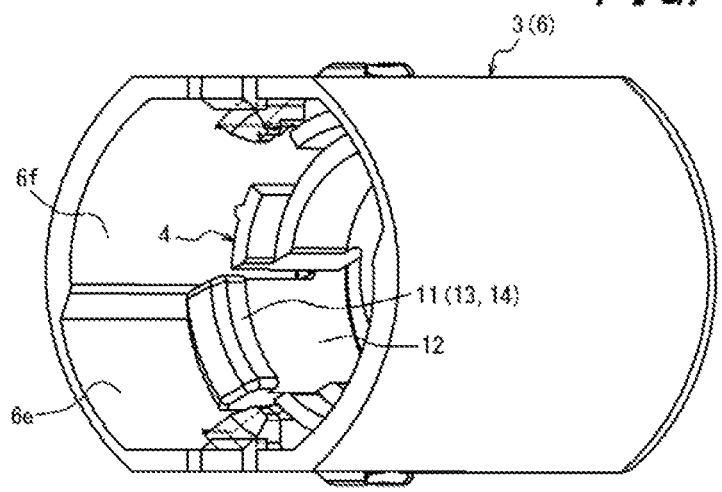
FIG. 11A is a perspective view illustrating the covering member and the locking member in the state at the time of starting connection illustrated in FIG. 5 when viewed from a different angle.
Figure 11B:
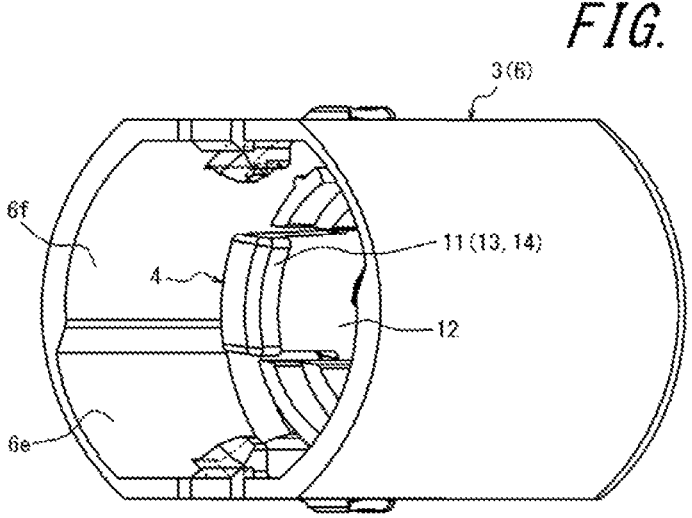
FIG. 11B is a perspective view illustrating the covering member and the locking member in a state between the state at the time of starting connection illustrated in FIG. 5 and the state at the time of completing connection illustrated in FIG. 6 when viewed from the different the other angle.
Figure 11C:
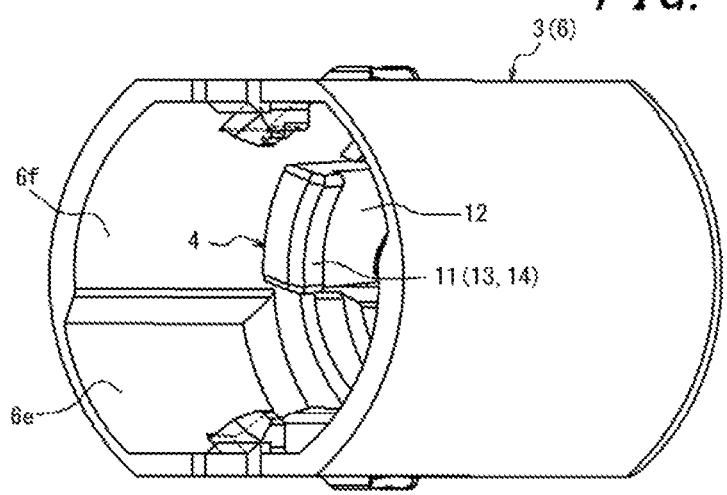
FIG. 11C is a perspective view illustrating the covering member and the locking member in the state at the time of completing connection illustrated in FIG. 6 when viewed from the different angle.

Furthermore, in the present embodiment, when the locking member 4 is rotated in the first rotating direction with respect to the covering member 6 as illustrated in FIGS. 11A to 11C in order to elastically deform the plurality of elastic members 12 of the locking member 4, each of the plurality of elastic members 12 is elastically deformed radially inward along with movement from the first inner diameter portion 6e to the second inner diameter portion 6f, and each of the plurality of first engagement portions 13 is engaged with the female connector portion 101 along with this elastic deformation (refer to FIGS. 6B and 11C).

Figure 11D:
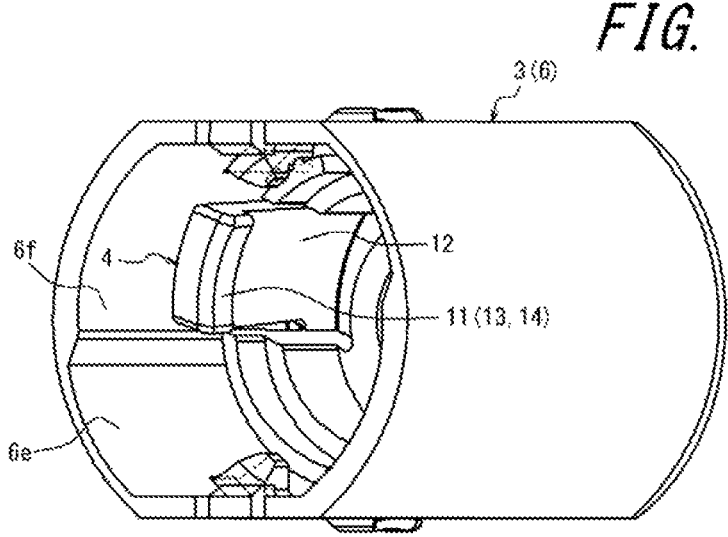
FIG. 11D is a perspective view of the covering member and the locking member in the state before releasing the first locked state after releasing the second locked state illustrated in FIG. 8 when viewed from the different angle.
Figure 12D:
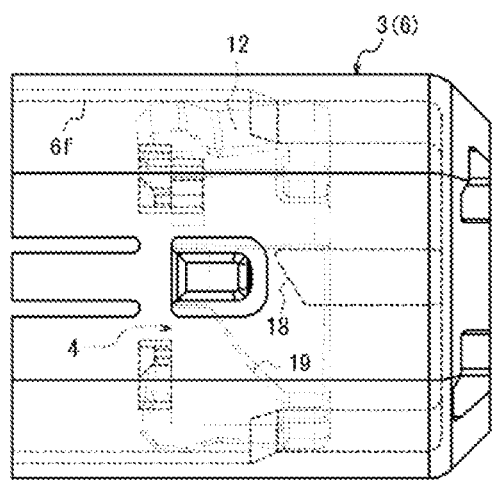
FIG. 12D is a side view illustrating the covering member and the locking member in the state before releasing the first locked state after releasing the second locked state illustrated in FIG. 8.

Furthermore, in the present embodiment, when the locking member 4 is moved to the distal end side (front side) with respect to the covering member 6 from this state, the locking member 4 is moved without being rotated while the plurality of elastic members 12 is kept being located at the second inner diameter portion 6f as illustrated in FIGS. 10D, 11D, and 12D. Therefore, when the locking member 4 is moved to the distal end side (front side) with respect to the covering member 6, elastic deformation of the plurality of elastic members 12 is maintained and the engaged state between the plurality of first engagement portions 13 and the female connector portion 101, namely, the first locked state is maintained (refer to FIG. 8B).

Figure 9A:
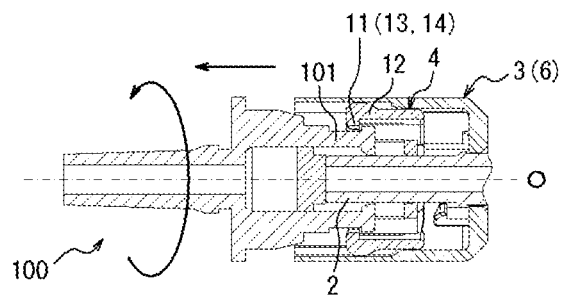
FIGS. 9A-9D depict a state at the time of completing disconnection for the medical connector illustrated in FIGS. 1A-1D and the other medical connector, FIG. 9A being a partial cross-sectional view taken along a line A-A in FIG. 9D.
Figure 9B:
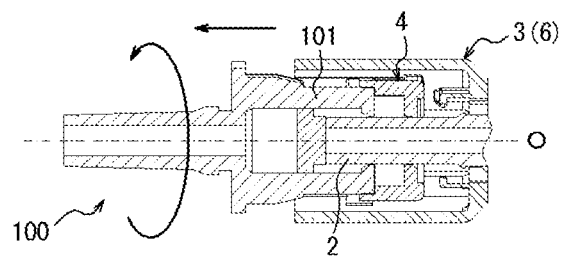
Figure 9C:
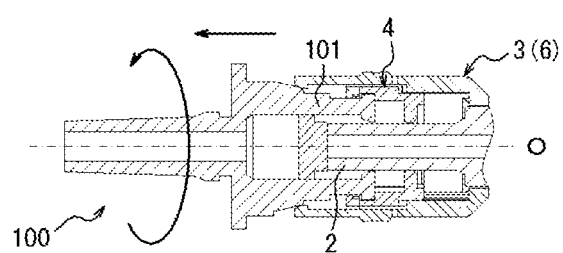
Figure 9D:
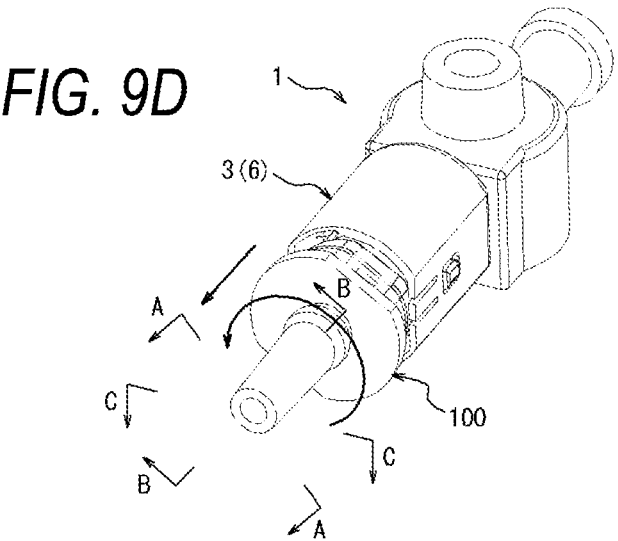

Additionally, in the present embodiment, when the locking member 4 is rotated in the second rotating direction with respect to the covering member 6 from this state (refer to FIGS. 11D and 12D), each of the plurality of elastic members 12 is moved from the second inner diameter portion 6f to the first inner diameter portion 6e as illustrated in FIGS. 11A and 12A and restored radially outward along with this movement, and engagement between each of the plurality of first engagement portions 13 and the female connector portion 101 is disengaged along with this restoration (refer to FIG. 9A). Meanwhile, the locking member 4 is rotated in the second rotating direction by a mechanism in which the plurality of first engagement protruding portions 14 (refer to FIG. 8B) is pushed with end edges 103a of the plurality of first engagement recessed portions 103 of the female connector portion 101 illustrated in FIG. 1 by rotating the female connector portion 101 in the second rotating direction.

Meanwhile, the plurality of elastic members (two in the present example) extending from the partition wall portion 6b to the distal end side is provided at the covering member 6 as illustrated particularly in FIG. 4, and a plurality of third engagement protruding portions 20 (two in the present example) that can be engaged with the locking member 4 is provided on the distal end sides of the elastic members. Additionally, when the locking member 4 reaches an end portion on the proximal end side of the movable range inside the covering member 6, the plurality of third engagement protruding portions 20 is engaged with the plurality of opening portions 21 (two in the present example) (refer to FIG. 3) of the locking member 4, thereby giving sense of moderation (refer to FIG. 6B), and also, when the locking member 4 is separated from the end portion on the proximal end side, engagement between the plurality of third engagement protruding portions 20 and the plurality of opening portions 21 of the locking member 4 is released, thereby giving sense of moderation (refer to FIG. 8B).

Additionally, a plurality of fourth engagement protruding portions 22 (two in the present example) is provided on the inner peripheral surface of the outer peripheral wall portion 6a of the covering member 6 as illustrated in FIGS. 4, 10A, and 10D. Furthermore, the locking member 4 is provided with a plurality of fifth engagement protruding portions 23 (two in the present example) that can be engaged with the plurality of fourth engagement protruding portions 22 (refer to FIG. 10D). Additionally, when the locking member 4 is rotated in the second rotating direction with respect to the covering member 6 after the locking member 4 reaches an end portion on the distal end side of the movable range inside the covering member 6 (in other words, when a state is changed from the state in FIG. 10D to the state in FIG. 10A), the plurality of fifth engagement protruding portions 23 passes over the plurality of fourth engagement protruding portions 22, thereby giving sense of moderation.

Meanwhile, particularly as illustrated in FIG. 1A, while a flow path is formed in an opening portion of the female connector portion 101 of the other medical connector 100 by opening the opening portion when the male connector portion 2 of the medical connector 1 is inserted, a valve body 105 adapted to close the opening portion is provided when the male connector portion 2 is not inserted. In the present example, biasing force is applied to a top surface portion 105a of the valve body 105 from the flow path side to a top surface portion side of the female connector portion 101. While a specific structure to generate such biasing force is not illustrated, examples of such a structure may be obtained by, for example, arranging a helical spring separately from the valve body 105 inside the flow path or by providing a bellows-like elastic portion integrally with the top surface portion 105a of the valve body 105.

Furthermore, while a specific structure to form the flow path by the valve body 105 opening the opening portion of the female connector portion 101 at the time of inserting the male connector portion 2 of the medical connector 1 is not illustrated, such a structure can be obtained by, for example, suitably providing the valve body 105 or a housing of the female connector portion 101 with a groove that sections a part of the flow path formed at the time of opening the opening portion of the female connector portion 101.

As described above, the medical connector 1 according to the present embodiment includes: the connector body 1a including the male connector portion 2 and the cover portion 3 surrounding the outer periphery of the male connector portion 2; the locking member 4 arranged inside the cover portion 3, movable only within the predetermined range in the direction along the axis line O of the male connector portion 2 with respect to the cover portion 3, and also including the first locking portion 11; the second locking portion 15; and the second unlock operating portion 16. Furthermore, the first locking portion 11 is engaged with the female connector portion 101 of the other medical connector 100, and can bring the female connector portion 101 into the first locked state. Additionally, the second locking portion 15 can bring, while in the first locked state, the female connector portion 101 into the second locked state in which the female connector portion 101 cannot be moved in the disengagement direction with respect to the male connector portion 2, and the second unlock operating portion 16 is an operating portion to release the second locked state.

Furthermore, the medical connector 1 is adapted to have a structure in which: when the male connector portion 2 is inserted into the female connector portion 101, the first locking portion 11 is engaged with the female connector portion 101 and the female connector portion 101 is brought into the first locked state and also into the second locked state.

Moreover, the medical connector 1 is adapted to have a structure in which: when the second locked state is released by operation of the second unlock operating portion 16 and the female connector portion 101 is moved in the disengagement direction with respect to the male connector portion 2, the locking member 4 is moved in the disengagement direction together with the female connector portion 101 while keeping the first locked state; and when the female connector portion 101 is rotated with respect to the male connector portion 2, the first locked state is released.

Therefore, according to the medical connector 1 of the present embodiment, when the male connector portion 2 is inserted into the female connector portion 101, the first locking portion 11 is engaged with the female connector portion 101, and the female connector portion 101 is brought into the first locked state and also into the second locked state. Therefore, according to the present embodiment, the connectors 1 and 100 can be connected only by inserting the male connector portion 2 into the female connector portion 101 of the other medical connector 100. Additionally, since the first locking portion 11 is located inside the cover portion 3 in the connected state, unintended disengagement of the connectors 1 and 100 caused by external force acting on the first locking portion 11 can be prevented.

Further, according to the medical connector 1 of the present embodiment, when the second locked state is released by operating the second unlock operating portion 16 from the connected state of the connectors 1 and 100 and the female connector portion 101 is moved in the disengagement direction with respect to the male connector portion 2, the locking member 4 is moved in the disengagement direction together with the female connector portion 101 while keeping the first locked state, and when the female connector portion 101 is rotated with respect to the male connector portion 2, the first locked state can be released.

Thus, in the present embodiment, the three-step operation including operation of the second unlock operating portion 16, pulling operation of the female connector portion 101, and rotating operation of the female connector portion 101 are needed to be performed in order to release connection between the connectors 1 and 100.

Therefore, according to the medical connector 1 of the present embodiment, it is possible to more surely prevent unintended disengagement while securing easiness of connecting operation to the other medical connector 100.

Additionally, the medical connector 1 according to the present embodiment is adapted to have a structure in which: when the male connector portion 2 is inserted into the female connector portion 101, the locking member 4 is pushed by the female connector portion 101 and moved to the proximal end side of the male connector portion 2; the locking member 4 is elastically deformed along with this movement; the first locking portion 11 is engaged with the female connector portion 101 along with this elastic deformation; the locking member 4 is rotated together with the female connector portion 101 when the female connector portion 101 is rotated with respect to the male connector portion 2 at the time of releasing the first locked state; the locking member 4 is restored from the elastic deformation along with this rotation; and the first locked state is released along with this restoration.

Therefore, according to the medical connector 1 of the present embodiment, the female connector portion 101 can be brought into the first locked state and the first locked state can be released by the simple structure.

Furthermore, the medical connector 1 according to the present embodiment is adapted to have a structure in which: when the male connector portion 2 is inserted into the female connector portion 101, the locking member 4 is pushed by the female connector portion 101 and moved to the proximal end side of the male connector portion 2 while being rotated in the first rotating direction; and the direction in which the female connector portion 101 is rotated with respect to the male connector portion 2 at the time of releasing the first locked state is the second rotating direction that is the opposite direction of the first rotating direction.

Therefore, according to the medical connector 1 of the present embodiment, the female connector portion 101 can be brought into the first locked state and the first locked state can be released by the simple structure.

Furthermore, the medical connector 1 according to the present embodiment is adapted to have a structure in which: the first abutting surface 18 is provided on the inner peripheral surface of the cover portion 3; the second abutting surface 19 is provided on the outer peripheral surface of the locking member 4; at least one of the first abutting surface 18 and the second abutting surface 19 is formed along a helical trajectory; and the locking member 4 is rotated in the first rotating direction with respect to the male connector portion 2 when the second abutting surface 19 is pressed against the first abutting surface 18.

Therefore, according to the medical connector 1 of the present embodiment, the locking member 4 can be rotated by the simple structure.

Moreover, the medical connector 1 according to the present embodiment is adapted to have a structure in which: the first locking portion 11 is formed as a plurality of first engagement portions 13 provided on the distal end sides of the plurality of elastic members 12; the first inner diameter portion 6e having the first inner diameter and the second inner diameter portion 6f having the second inner diameter more reduced than that of the first inner diameter portion 6e are provided on the inner peripheral surface of the cover portion 3; when the locking member 4 is pushed by the female connector portion 101 and moved to the proximal end side of the male connector portion 2, each of the plurality of elastic members 12 is elastically deformed radially inward along with movement from the first inner diameter portion 6e to the second inner diameter portion 6f; and each of the plurality of first engagement portions 13 is engaged with the female connector portion 101 along with this elastic deformation.

Therefore, according to the medical connector 1 of the present embodiment, the locking member 4 can be elastically deformed and the first locking portion 11 can be engaged with the female connector portion 101 by the simple structure.

Additionally, the medical connector 1 according to the present embodiment is adapted to have a structure in which: the plurality of first engagement portions 13 is provided as the plurality of first engagement protruding portions 14 provided on the distal end sides of the plurality of elastic members 12 and protruding radially inward; and the plurality of first engagement protruding portions 14 can be engaged with the plurality of first engagement recessed portions 103 provided in a recessed manner on the outer peripheral surface 102 of the female connector portion 101.

Therefore, according to the medical connector 1 of the present embodiment, the plurality of first engagement portions 13 can be more surely engaged with the female connector portion 101 by the simple structure.

Additionally, the medical connector 1 according to the present embodiment is adapted to have a structure in which the second locking portion 15 brings the female connector portion 101 into the second locked state by engaging the female connector portion 101 with the cover portion 3.

Therefore, according to the medical connector 1 of the present embodiment, the second locking portion 15 can be achieved by the simple structure.

Furthermore, the medical connector 1 according to the present embodiment is adapted to have a structure in which: the second locking portion 15 is formed of the second engagement protruding portion 15a provided at the cover portion 3 and protruding radially inward; the second engagement protruding portion 15a can be engaged with the second engagement recessed portion 104 provided in a recessed manner on the outer peripheral surface 102 of the female connector portion 101; and the second unlock operating portion 16 is the operating portion of the swing lever 17 including the second engagement protruding portion 15a and also integrally provided on the cover portion 3.

Therefore, according to the medical connector 1 of the present embodiment, the second unlock operating portion 16 can be achieved by the simple structure.

The above description merely illustrates one embodiment of the present invention, and various kinds of modifications can be made in the scope of claims. For example, in the above-described embodiment, it has been described that the second locking portion 15 is adapted to bring the female connector portion 101 into the second locked state by engaging the female connector portion 101 with the cover portion 3, but not limited thereto, for example, the female connector portion 101 may be brought into the second locked state by engaging the locking member 4 with the cover portion 3.

REFERENCE NUMERAL LIST

1 Medical connector
1a Connector body
2 Male connector portion
3 Cover portion
4 Locking member
5 Housing
6 Covering member
6a Outer peripheral wall portion
6b Partition wall portion
6c Through hole
6d Protrusion
6e First inner diameter portion
6f Second inner diameter portion
7 Female connector portion
8 Mixed injection port portion
8a Valve body
9 Distal-end side stopper portion
10 Proximal-end side stopper portion
11 First locking portion
12 Elastic piece
19 First engagement portion (first locking portion)
14 First engagement protruding portion (first locking portion)
15 Second locking portion
15a Second engagement protruding portion (second locking portion)
16 Second unlock operating portion
17 Swing lever
18 First abutting surface
19 Second abutting surface
20 Third engagement protruding portion
21 Opening portion
22 Fourth engagement protruding portion
23 Fifth engagement protruding portion
100 The other medical connector
101 Female connector portion of the other medical connector
102 Outer peripheral surface of female connector portion of the other medical connector
103 First engagement recessed portion (engagement recessed portion for first locking portion)
103a End edge of first engagement recessed portion
104 Second engagement recessed portion (engagement recessed portion for second locking portion)
105 Valve body
105a Top surface portion of valve body
O Axis line

What is claimed is:

1. A medical connector comprising:
   a connector body comprising a male connector portion and a cover portion surrounding an outer periphery of the male connector portion;
   a locking member located inside the cover portion and being movable with respect to the cover portion within a predetermined range in a direction along an axis of the male connector portion, the locking member comprising a first locking portion;
   a second locking portion; and
   an unlock operating portion;
   wherein the first locking portion is configured to engage with a female connector portion of another medical connector and to bring the female connector portion into a first locked state,
   wherein the second locking portion is configured to, while the female connector portion is in the first locked state, bring the female connector portion into a second locked state in which the female connector portion cannot be moved in a disengagement direction with respect to the male connector portion,
   wherein the unlock operating portion is configured to release the female connector portion from the second locked state,
   wherein, when the male connector portion is inserted into the female connector portion, the female connector portion is brought into the first locked state and the second locked state,
   wherein, when the second locked state is released by operation of the unlock operating portion, and the female connector portion is moved in the disengagement direction with respect to the male connector portion, the locking member is moved in the disengagement direction together with the female connector portion while the first locked state is maintained, and
   wherein, when the female connector portion is rotated with respect to the male connector portion, the first locked state is released.

2. The medical connector according to claim 1, wherein:
   when the male connector portion is inserted into the female connector portion, the locking member is pushed by the female connector portion and undergoes movement to a proximal end side of the male connector portion, the locking member undergoes elastic deformation along with the movement of the locking member to the proximal end side of the male connector portion, and the first locking portion is engaged with the female connector portion along with the elastic deformation of the locking member, and when the female connector portion is rotated with respect to the male connector portion at the time of releasing the first locked state, the locking member undergoes rotation together with the female connector portion, the locking member undergoes restoration from the elastic deformation along with the rotation of the locking member, and the first locked state is released along with the restoration of the locking member.

3. The medical connector according to claim 2, wherein:
when the male connector portion is inserted into the female connector portion, the locking member is pushed by the female connector portion and is moved to the proximal end side of the male connector portion while being rotated in a first rotating direction, and
a direction in which the female connector portion is rotated with respect to the male connector portion at the time of releasing the first locked state is a second rotating direction that is opposite the first rotating direction.

4. The medical connector according to claim 3, wherein:
a first abutting surface is located on an inner peripheral surface of the cover portion,
a second abutting surface is located on an outer peripheral surface of the locking member,
at least one of the first abutting surface and the second abutting surface is formed along a helical trajectory, and
when the second abutting surface is pressed against the first abutting surface, the locking member is rotated in the first rotating direction with respect to the male connector portion.

5. The medical connector according to claim 4, wherein the second locking portion is configured to bring the female connector portion into the second locked state by engaging the female connector portion with the cover portion.

6. The medical connector according to claim 5, wherein:
the second locking portion comprises an engagement protruding portion located at the cover portion and protruding radially inward,
the engagement protruding portion is configured to be engaged with an engagement recessed portion on an outer peripheral surface of the female connector portion,
the engagement protruding portion is a part of a swing lever that is integrally formed with the cover portion; and
the unlock operating portion is an operating portion of the swing lever.

7. The medical connector according to claim 4, wherein the locking member comprises a plurality of elastic members,
the first locking portion comprises a plurality of engagement portions provided on distal end sides of the plurality of elastic members,
a first inner diameter portion having a first inner diameter and a second inner diameter portion having a second inner diameter less than the first inner diameter are located on the inner peripheral surface of the cover portion, and
when the locking member is pushed by the female connector portion and moved to the proximal end side of the male connector portion, each of the plurality of elastic members is elastically deformed radially inward along with movement from the first inner diameter portion to the second inner diameter portion, and the first locking portion is engaged with the female connector portion along with the elastic deformation of the plurality of elastic members.

8. The medical connector according to claim 7, wherein:
the plurality of engagement portions protrude radially inward, and
the plurality of engagement portions are configured to engage with a plurality of engagement recessed portions on an outer peripheral surface of the female connector portion.

9. The medical connector according to claim 8, wherein the second locking portion is configured to bring the female connector portion into the second locked state by engaging the female connector portion with the cover portion.

10. The medical connector according to claim 9, wherein:
the second locking portion comprises an engagement protruding portion located at the cover portion and protruding radially inward,
the engagement protruding portion is configured to be engaged with an engagement recessed portion on the outer peripheral surface of the female connector portion,
the engagement protruding portion is a part of a swing lever that is integrally formed with the cover portion; and
the unlock operating portion is an operating portion of the swing lever.

11. The medical connector according to claim 7, wherein the second locking portion is configured to bring the female connector portion into the second locked state by engaging the female connector portion with the cover portion.

12. The medical connector according to claim 11, wherein:
the second locking portion comprises an engagement protruding portion located at the cover portion and protruding radially inward,
the engagement protruding portion is configured to be engaged with an engagement recessed portion on an outer peripheral surface of the female connector portion,
the engagement protruding portion is a part of a swing lever that is integrally formed with the cover portion; and
the unlock operating portion is an operating portion of the swing lever.

13. The medical connector according to claim 2, wherein the locking member comprises a plurality of elastic members,
the first locking portion comprises a plurality of engagement portions provided on distal end sides of the plurality of elastic members,
a first inner diameter portion having a first inner diameter and a second inner diameter portion having a second inner diameter less than the first inner diameter are located on an inner peripheral surface of the cover portion, and
when the locking member is pushed by the female connector portion and moved to the proximal end side of the male connector portion, each of the plurality of elastic members is elastically deformed radially inward along with movement from the first inner diameter portion to the second inner diameter portion, and the first locking portion is engaged with the female connector portion along with the elastic deformation of the plurality of elastic members.

14. The medical connector according to claim 13, wherein:
the plurality of engagement portions protrude radially inward, and
the plurality of engagement portions are configured to engage with a plurality of engagement recessed portions on an outer peripheral surface of the female connector portion.

15. The medical connector according to claim 3, wherein the locking member comprises a plurality of elastic members,
the first locking portion comprises a plurality of engagement portions provided on distal end sides of the plurality of elastic members,
a first inner diameter portion having a first inner diameter and a second inner diameter portion having a second inner diameter less than the first inner diameter are located on an inner peripheral surface of the cover portion, and
when the locking member is pushed by the female connector portion and moved to the proximal end side of the male connector portion, each of the plurality of elastic members is elastically deformed radially inward along with movement from the first inner diameter portion to the second inner diameter portion, and the first locking portion is engaged with the female connector portion along with the elastic deformation of the plurality of elastic members.

16. The medical connector according to claim 15, wherein:
the plurality of engagement portions protrude radially inward, and
the plurality of engagement portions are configured to engage with a plurality of engagement recessed portions on an outer peripheral surface of the female connector portion.

17. The medical connector according to claim 1, wherein the second locking portion is configured to bring the female connector portion into the second locked state by engaging the female connector portion with the cover portion.

18. The medical connector according to claim 17, wherein:
the second locking portion comprises an engagement protruding portion located at the cover portion and protruding radially inward,
the engagement protruding portion is configured to be engaged with an engagement recessed portion on an outer peripheral surface of the female connector portion,
the engagement protruding portion is a part of a swing lever that is integrally formed with the cover portion; and
the unlock operating portion is an operating portion of the swing lever.

19. A method of connecting a medical connector to another medical connector, the method comprising:
providing a medical connector comprising:
a connector body comprising a male connector portion and a cover portion surrounding an outer periphery of the male connector portion;
a locking member located inside the cover portion and being movable with respect to the cover portion within a predetermined range in a direction along an axis of the male connector portion, the locking member comprising a first locking portion;
a second locking portion; and
an unlock operating portion;
wherein the first locking portion is configured to engage with a female connector portion of said another medical connector and to bring the female connector portion into a first locked state,
wherein the second locking portion is configured to, while the female connector portion is in the first locked state, bring the female connector portion into a second locked state in which the female connector portion cannot be moved in a disengagement direction with respect to the male connector portion, and
wherein the unlock operating portion is configured to release the female connector portion from the second locked state;
inserting the male connector portion into the female connector portion such that the female connector portion is brought into the first locked state and the second locked state;
releasing the second locked state by operating the unlock operating portion, and moving the female connector portion in the disengagement direction with respect to the male connector portion, such that the locking member is moved in the disengagement direction together with the female connector portion while the first locked state is maintained; and
rotating the female connector portion with respect to the male connector portion such that the first locked state is released.

\* \* \* \* \*